United States Patent [19]

Danieletto et al.

[11] E Patent Number: Re. 31,809

[45] Reissued Date of Patent: Jan. 22, 1985

[54] EXTERNAL AXIAL FIXATION UNIT

[75] Inventors: Giuseppina Danieletto; Giovanni De Bastiani, both of Verona; Giovanni Faccioli, Monzambano; Lodovico R. Brivio, Castenedola; Roberto Aldegheri, San Giovanni Lupatoto; Andrea Cavazzana, Verona, all of Italy

[73] Assignee: Orthofix S.r.l., Verona, Italy

[21] Appl. No.: 482,586

[22] Filed: Apr. 6, 1983

Related U.S. Patent Documents

Reissue of:

[64] Patent No.: 4,312,336
Issued: Jan. 26, 1982
Appl. No.: 93,897
Filed: Nov. 13, 1979

[30] Foreign Application Priority Data

Nov. 10, 1978 [IT] Italy ..... 84949 A/78
Apr. 5, 1979 [IT] Italy ..... 84930 A/79

[51] Int. Cl.[3] ..... A61F 5/04

[52] U.S. Cl. ..... 128/92 A; 128/92 B; 403/90; 403/56; 403/137

[58] Field of Search ..... 128/92 A, 92 B, 92 BB, 128/92 BA, 92 R; 403/90, 56, 137

[56] References Cited

U.S. PATENT DOCUMENTS

| | | | |
|---|---|---|---|
| 2,121,525 | 6/1938 | Johnson | 403/90 |
| 2,346,346 | 4/1944 | Anderson | 128/92 A |
| 2,382,019 | 8/1945 | Miller | 128/92 B |
| 2,612,159 | 9/1952 | Collison | 128/92 BA |
| 2,702,543 | 2/1955 | Pugh et al. | 128/92 BA |
| 2,760,488 | 8/1956 | Pierce | 128/92 A |
| 3,051,169 | 8/1962 | Grath | 128/92 BB |
| 3,059,948 | 10/1962 | Thompson et al. | 403/90 |
| 3,211,405 | 10/1965 | Fey et al. | 403/90 |
| 3,841,769 | 10/1974 | Bowerman | 403/90 |
| 3,842,825 | 10/1974 | Wagner | 128/92 B |
| 4,059,102 | 11/1977 | Devas | 128/92 B |
| 4,135,505 | 1/1979 | Day | 128/92 A |
| 4,187,841 | 2/1980 | Knutson | 128/92 A |

OTHER PUBLICATIONS

Webster's 3rd New International Dictionary, p. 1005 re "grub screw".

*Primary Examiner*—C. Fred Rosenbaum
*Assistant Examiner*—C. W. Shedd
*Attorney, Agent, or Firm*—Hopgood, Calimafde, Kalil, Blaustein & Judlowe

[57] ABSTRACT

Apparatus for the external setting or securing of the parts of a fractured bone, comprising an elongate central body member comprised of two parts mutually displaceable parallel to the longitudinal axis of said member, whereby each part of the central body member supports a clamping device for the pins to be inserted into a part of the bone. The two mutually displaceable parts are engaged by a pressing and tensioning device causing the mutual longitudinal displacement of the part. When the pins are inserted in the bone parts to be pressed together, the pressing and tensioning device is actuated until the two bone sections abut against each other at the required pressure. Then the securing devices fix the two parts of the central body member into their position. Subsequently, the pressing and tensioning device is removed from the central body member since it is no longer required. For reliable guidance the two parts of the central body member are telescopically inserted one within the other and universal joints are provided between the central body member and the clamping devices for compensation. These universal joints after being mounted on the bone to be put in splints are adapted to be fixed by fixing devices, so that a completely stable position of the whole apparatus is provided. The pins to be inserted into the bone parts for reliable anchorage, in view of the tractive forces occurring at least in the section of the pin insertable in the bone, are provided with an external thread.

22 Claims, 21 Drawing Figures

17
35
28
25
27
21
19
22
24
23
13
40
16
38
12
41
45
37
10
14
29
13'
16'

EXTERNAL AXIAL FIXATION UNIT

Matter enclosed in heavy brackets [ ] appears in the original patent but forms no part of this reissue specification; matter printed in italics indicates the additions made by reissue.

The present invention relates to an apparatus for the external setting or securing of the parts of a fractured bone, said apparatus comprising an elongate central body member comprised of two parts which are mutually displaceable parallel to the longitudinal axis of said member, whereby each part of the central body member supports a clamping device for the pins to be inserted into a part of the bone, and having a pressing and tensioning device in engagement with both parts of the central body member for causing the mutual longitudinal displacement of the two parts of the central body member.

Known apparatus of this kind are relatively heavy and require considerable space. More particularly, such apparatus does not ensure that there is a desired certain clearance between the bone and the pins of the device inserted therein, and accordingly the stability of the bone securing apparatus is considerably reduced. Above all, with the apparatus being mounted on a fractured bone for a long time the repeated muscle contractions of the associated limb causes a slackening of such apparatus, which has an adverse effect on the strength of the apparatus and hence on the healing process.

The present invention has as an object to provide an improved apparatus of the type referred to above so that, even with long-term use such improved apparatus remains absolutely secure. Moreover, such improved apparatus is light weight and requires little space. More especially, any displacement between the bone and the improved apparatus along the axis of the pins should be impossible provided there is clearance between the bone and the pins. Furthermore, the pins are so formed that any play arising between the bone and the pins is prevented at the time of insertion of the pins into the bone. Even if the pins are mounted on both sides of the fracture surface of the bone in different planes, the apparatus should satisfactorily and durably locate the bone.

According to the present invention there is provided apparatus for the external setting or securing of the parts of a fractured bone, said apparatus comprising an elongate central body member which is comprised of two parts adapted to be mutually displaced parallel to the longitudinal axis of said member whereby each part of the central body member supports a clamping device for the pins to be inserted into a part of the bone, and having a pressing and tensioning device (*e.g., a turnbuckle or a screw jack*) in engagement with both parts of the central body member, in which the two parts of the central body member are telescopically inserted one within the other, in which the clamping devices, by means of a universal ball joint, are mounted on the associated part of the central body member and the mutual position of the parts of the central body member is fixable by securing devices, in which the pressing and tensioning device is removably connected to the parts of the central body member and in which the pins, at least in the section insertable in the bone have an external thread.

By the combination of these features, an extremely simple, light weight apparatus requiring little space is provided which ensures an absolutely secure and durable mounting of the apparatus on the fractured bone. Location of the clamping devices supporting the pins by means of universal joints which may be fixed in any direction pivotal and rotatable and subsequently in the required securing position, permit a maximum adaptation of the apparatus to the bone to be set. Fixing of both parts of the central body member after setting the necessary pressure at the fracture point of the bone, permits a subsequent removal of the pressing and tensioning device, whereby the weight of the apparatus remaining on the limb to be put in splints and its space requirement are substantially reduced. Loosely fitting pins in the bone, which cause slackening of the whole apparatus during use, is prevented by the use of self-tapping external thread on the pins. Especially by this means occurrence of micro-fractures of the bone during insertion of the pins into the bone is prevented.

The present invention will be further illustrated by way of example, with reference to the accompanying drawings, in which.

The various Figures are drawn on different scales. Identical reference numerals are used to correspond to identical or equivalent parts in different Figures.

Figures 1, 5:
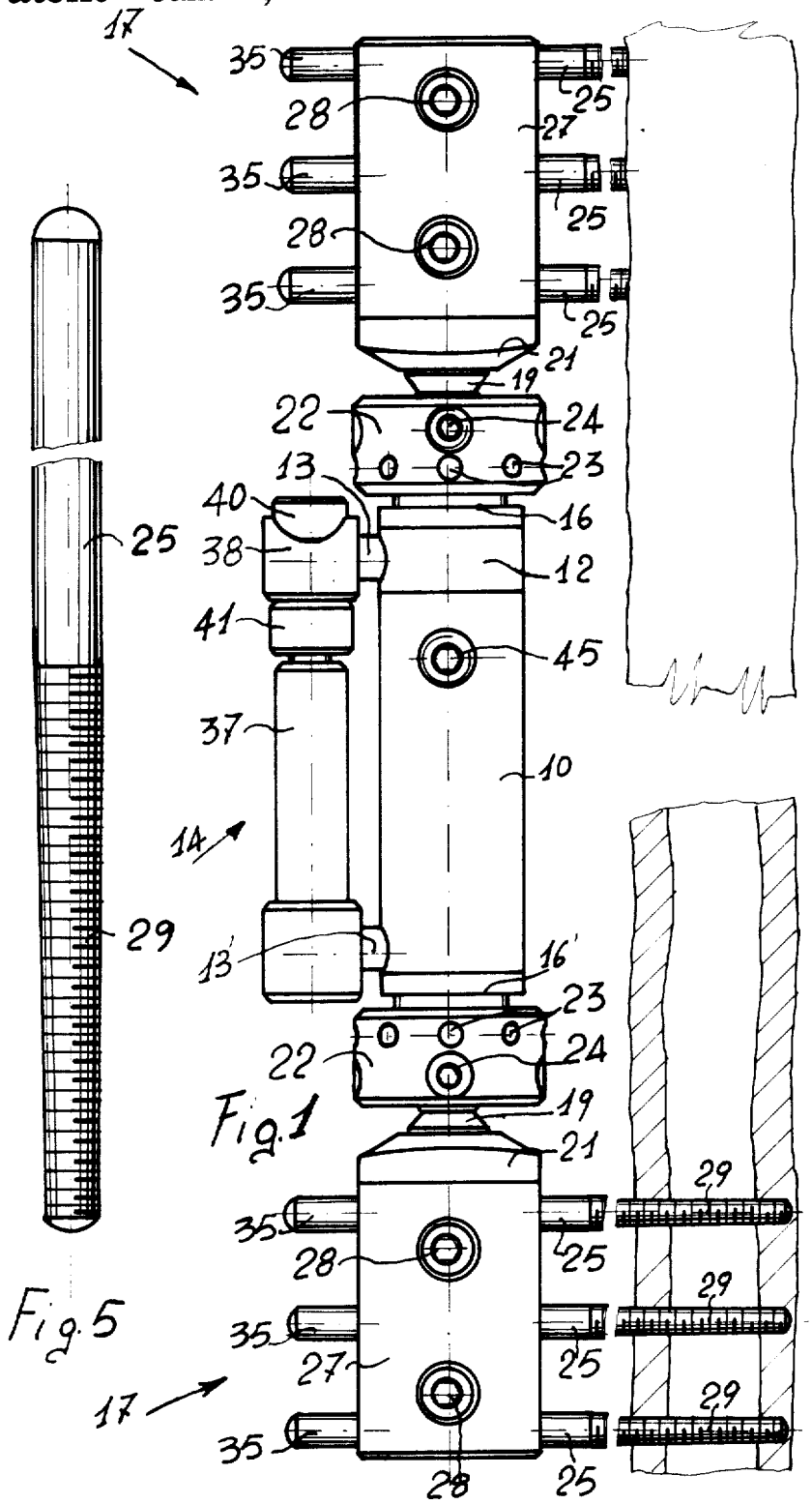
FIG. 1 is a schematic end view of an apparatus in accordance with the invention with partially interrupted pins, which are mounted on a partially interrupted bone, shown partially in elevation and partially in section.
FIG. 5 is a schematic view of a tapered pin.

The apparatus in accordance with the invention has a central body member which is comprised of an outer cylinder 10 in which a rod 11 is telescopically inserted, said rod 11 having a head 12 and the outer surface of the rod 11 corresponding to the inner surface of the cylinder 10, in which cylinder is provided the receiving bearing of a bolt 13 of the pressing and tensioning device 14.

Figure 2:
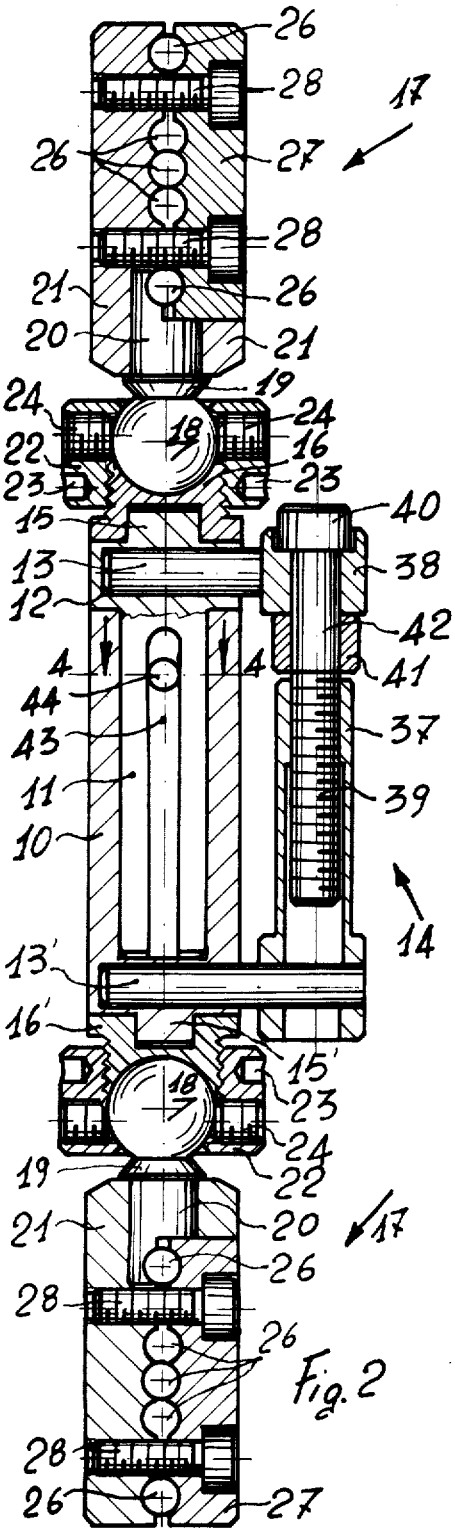
FIG. 2 is a vertical section through the apparatus of FIG. 1, turned through 180° and having clamping devices which are turned through 90° relative to the axis of the apparatus.

The upper part 15 of the head 12 is, in known manner, securely connected to a socket 16 which supports a spherical, segment-shaped, receiving seat for a ball 18, which ball, via a collar 19 and a rod 20 is secured to a fixed jaw 21 of a clamping device 17 supporting the pins. A threaded ring 22, which may be screwed onto the socket 16, anchors the ball 18 to the socket 16, whereby, however, before tightening the threaded ring 22, movements of the clamping device 17 relative to the longitudinal axis of the apparatus are permitted. The structure of the ball joint so formed is such that the center of rotation of ball 18 substantially lies on the longitudinal axis of the central body member as seen in FIG. 2. If the threaded ring 22 is screwed completely onto the socket 16 by means of a hook wrench, the projections of which may be inserted in the openings 23, the ball 18 may be secured against the socket 16; for greater reliability of location, screwbolts 24 are provided in the threaded ring 22, which, for example, may be tightened by a hexagonal spanner.

As soon as the shafts 25 of the pins are inserted in receiving seats 26, which are provided in the jaws of the clamping device 17, a displaceable jaw 27 is tightened against the fixed jaw 21 by means of screws 28.

In the base of the cylinder 10, similarly to the device on the head 12, the receiving seat of a bolt 13' of the pressing and tensioning device 14 is provided, whilst the lower part 15' of the cylinder 10 is securely connected to a socket 16'.

Figure 6:
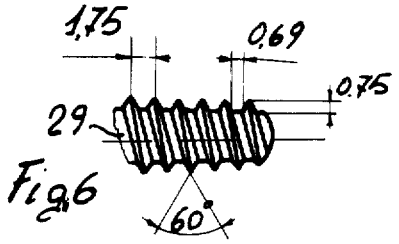
FIG. 6 is a schematic view of part of the thread of the tapered pin shown in FIG. 5.

With reference to FIG. 5, it is to be observed that the pin has a shaft 25 and a tapered core 29 with a conical thread, said thread, as shown in detail in FIG. 6, having a spirally extending thread profile, the conicity corresponding to that of the core 29 and having a constant pitch, so that the projection of the thread relative to the core, the inclination of the walls of the thread and the width of the grooves are constant. A tapered pin having the aforesaid properties is able to eliminate clearance which results in certain circumstances, between the bone and the pin due to an enlargement of the receiving cavity for the pin, which is to attributed to a yielding of the walls of the cavity and also consequent upon the tension or pressure to which the apparatus is subjected. Thus, by simply screwing the pin in further to the extent required, removes the clearance or play created.

It is clear that according to this embodiment, both the core of the pin and the thread due to their conicity contribute to removal of the clearance or play.

Figure 7:
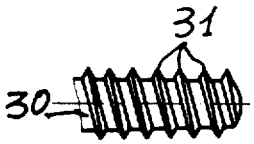
FIGS. 7 and 8 show two alternative embodiments of a part of the thread of a tapered pin in accordance with the invention.
Figure 8:
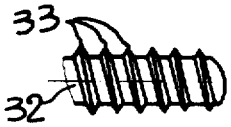
Figure 3:
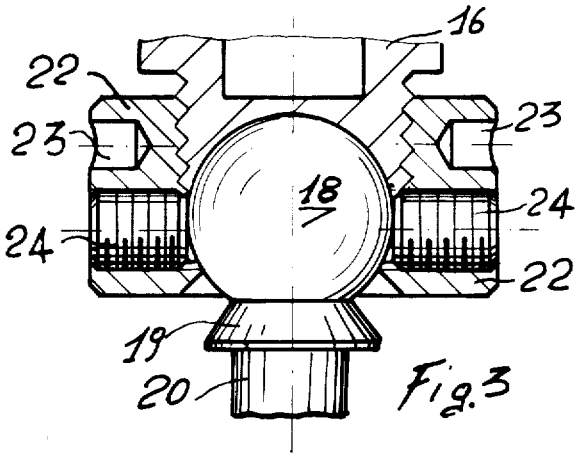
FIG. 3 is an enlarged section through a ball joint of a clamping device.

With reference to FIG. 7, the core 30 of the pin shown is tapered whilst the thread 31 extends in the form of a cylindrical screw or helix. In such instance, the core of the pin predominantly contributes to the removal of the clearance. In the alternative embodiment of FIG. 8, the contrary is the case, because the core 32 is cylindrical, whilst the thread 33 extends as a conical screw or helix. Thus, in this case the removal of clearance or play depends predominantly upon the thread.

It is clear that the three types of pins may be used with a single clamping device, even when the function developed thereby differs from one pin to the other. As an alternative to the arrangement shown in FIG. 5, the pin may have a core and a thread as described in connection with FIGS. 6, 7 and 8 penetrating only in the zones of the outer regions of the bone, whereby, however, the invention is not changed as to its essential features.

Moreover, it is clear that without this having been shown in the drawings, a pin in accordance with the invention may be partly provided with a known cylindrical core having a thread in the form of a cylindrical screw, in which the core and/or the thread tapers.

Practical tests with screws in accordance with the invention, carried out in bones of average cortical compactness, have led to excellent results with screws having a shaft of 6 mm $\phi$, having a core and/or thread with a conicity of 1:50, having a thread of 1.75 mm pitch, with an inclination of the walls of the thread of 60°, with a minimum width of groove of 0.69 mm and a thread depth of 0.75 mm, as shown in FIG. 6. However, it is to be understood that the present invention is not to be considered to be limited to such dimensions.

Figure 9:
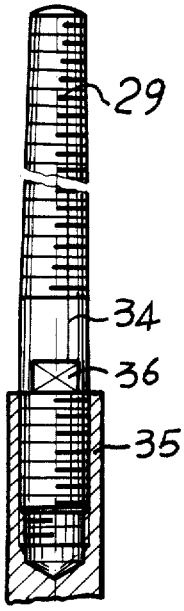
FIG. 9 is a schematic view of a tapered pin which is mounted in a suitable support member shown in section.

With particular reference to FIG. 9, the pins made as described above may have a shaft or a rod 34 which may be screwed into the cavity of a supporting member 35 which may be inserted between the jaws of the clamping device 17, so that the pins may be turned by a hook wrench, the hook of which may engage in openings 36, in order in this manner to remove the aforesaid clearance or play without having to slacken the jaws of the clamping device 17.

So as not to disturb the state of the installation during the removal of the clearance or play in the slightest way, it is extremely desirable that the pitch of the thread on the shaft corresponds accurately to the pitch of the thread in the core of the pin.

As soon as the pins are secured in the parts of the bone in planes above and below the fracture line, which may also differ from the sagital line or a plane extending through the longitudinal axis of the bone, the central portion of the apparatus is placed in a position in which its longitudinal axis extends parallel to the longitudinal axis of the bone, and the shafts of the pins or their supporting members are inserted into the receiving seats 26 of the jaws of the clamping devices 17, in order to subsequently secure the clamping devices relative to the central body member and the jaws of the clamping devices relative to the pins.

In this manner the apparatus is now in a position to exert pressure or tension on the bone by using the device 14, which device includes a hollow cylinder 37 to which the bolt 13' is secured at the lower end thereof, a second hollow cylinder 38 to which the bolt 13 is secured, a screw 39, the head 40 of which is mounted in the hollow cylinder 38 and a collar or sleeve 41 which is securely connected to a rod section 42 of the screw 39, the outer thread of which engages in the internal thread of the hollow cylinder 37. As soon as the bolts 13, 13' have been inserted in suitable cavities each formed in the parts 12 and 10, it suffices to screw in the screw 39 by actuating the head 40, in order, as required, to cause the mutual approach or separation of the parts 10 and 12 of the central body of the securing device with axial displacements of the rod 11 in the interior of the cylinder 10.

Figure 4:
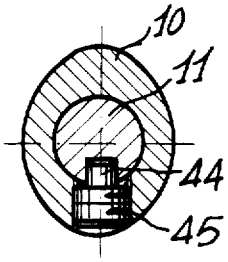
FIG. 4 is a section, vertical to the longitudinal axis of the apparatus, taken on the line 4—4 of FIG. 2.

The rod 11, see in this connection FIG. 2, has a groove 43 formed therein in which a stop and fixing pin or plug 44 projects. This pin 44, see FIG. 4 in this connection, is securely connected to a screw 45, the outer thread of which engages in the internal thread which is provided at a suitable point in cylinder 10. Thus, by virtue of the pin 44 projecting into groove 43, each of the two parts 10 and 11 of the central body member will be fixed against rotation with respect to the other part during longitudinal displacement of the two parts.

As soon as the required pressure or tension, which may be checked by a measuring scale, which is not shown, but which may be mounted on the rod 11, has been attained the screw 45 is tightened and the pin 44 caused to press against the bottom of the groove 43 and, by friction, the parts 10 and 12 of the central body member of the apparatus are secured both longitudinally and rotatively relative to each other. The device 14 may therefore be removed from the apparatus in that it is slackened and then the bolts 13–13' pulled out of the corresponding receiving seats.

It is clear that the last-described securing device may be replaced by through bores in the rod 11 and on the cylinder 10, into which stop and securing bolts may be inserted without departing from the scope of the invention.

Figure 12:
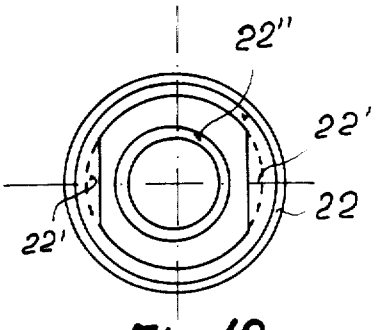
FIG. 12 is a view from below of a quick-release connector collar for locating the ball joint relative to the central body member of the apparatus.
Figure 10:
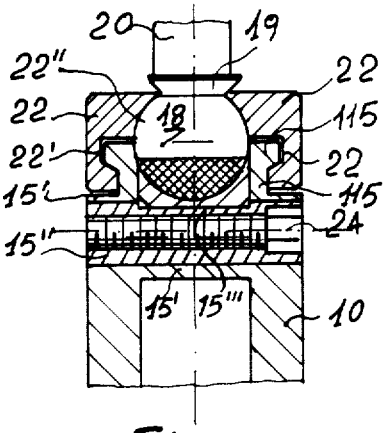
FIG. 10 is a section through a ball joint of a clamping device locatable by eccentric bolts.
Figure 11:
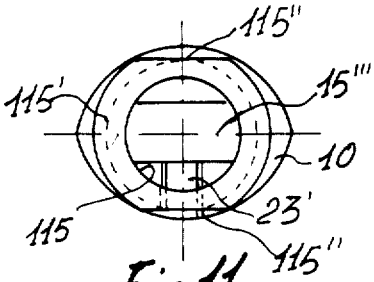
FIG. 11 is a plan view of an end portion of the cylindrical part of the central body member.

In accordance with FIGS. 10 to 12, a cylindrical pin 15'' is mounted in the end 15' of the cylinder 10; the cylindrical pin has a central portion 15''' which is eccentric relative to its ends.

The end 15' continues in a hollow cylinder 115 having an annular projection 115', which at 115'' is cut off along two parallel planes and which contact the surface of the hollow cylinder 115, whereby the severed positions 115'' permit the insertion and the subsequent rotary movement of a quick-release connector collar or sleeve 22 having an annular cavity 22' which is adapted in form locking arrangement relative to the annular projection 115''.

In the hollow cylinder 115, a cup or bowl 16' is mounted having a spherical cup-shaped receiving seat for the ball 18, which, via the collar 19 and the rod 20 is secured to the fixed jaw 21 of a clamping device supporting the pins, not shown, in accordance with the clamping device 17 shown in FIG. 1.

The lower part of cup 16' abuts against the eccentric part 15''' of the bolt 15'', for which reason after mounting the collar or sleeve 22 on the hollow cylinder 115, and after rotating it by a quarter turn in order to bring the annular projection 115' and the cavity 22' into engagement, the ball 18 is held secure between cup 16' having the spherical cup-shaped surface and a ring 22''.

The ball 18, whilst so retained, is still able to make a rotary movement, and is secured in any position in that the bolt 15'' is rotated so that, with its eccentric part 15''', it presses the cup 16' against the ball 18 and the latter against the ring 22''.

To increase the reliability of securing the ball 18, its outer surface may be partially or wholly provided with a knurling 18'; likewise the surfaces which come into contact with the ball 18 may also be provided with a knurling.

At one end of the bolt 15'' a hexagonal depression 24 is provided, the necessary rotary movements being imparted by a hexagonal spanner.

Figure 15:
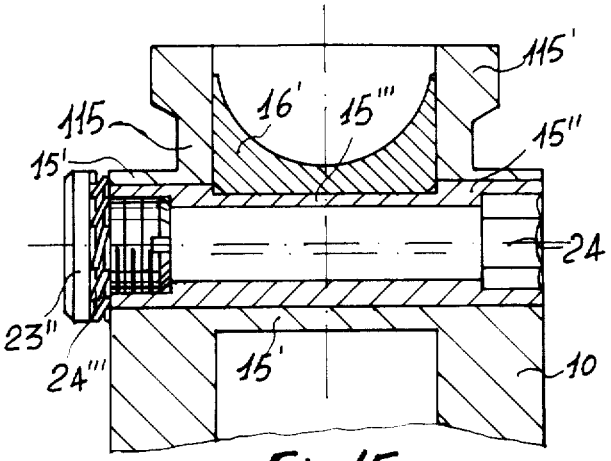
FIGS. 13, 14 and 15 show three embodiments of a securing device of the eccentric bolt.
Figure 13:
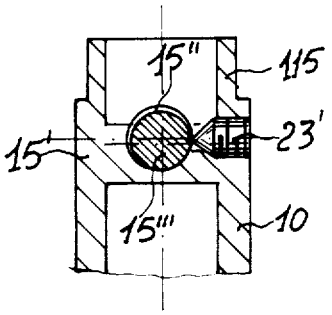
Figure 14:
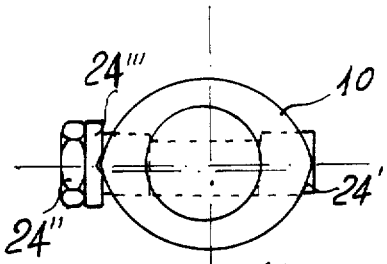

As soon as the ball 18 has been secured, the position of the bolt 15'' is fixable by means of a set screw 23' which, as shown in FIG. 13, is adapted to contact and fix the eccentric part 15'''. Such positioning may be assisted by securing the bolt 15'' by a nut 24' and a lock nut 24'', whereby a spring ring 24''', as shown by FIG. 14 is interposed, or by the tensional action of a screw 24'', via spring ring or washer 24''' placed on the bolt 15'' which cannot be laterally pulled out since the cup 16' prevents this and which with its lower part is supported on the eccentric part 15''', in accordance with FIG. 15.

Figure 16:
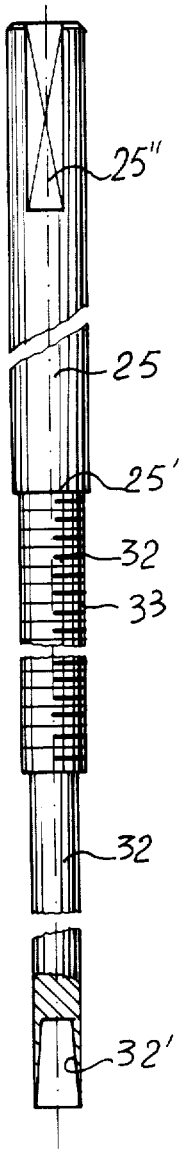
FIG. 16 is a partially interrupted and partially sectioned view of a pin which is suited to receive a removable tip in the form of a drill.

In the pins which are to be used with the two-sided securing device as shown in FIG. 16, the shank or shaft 25 has a diameter which is slightly larger than that of the core 32 and the thread 33, so that an annular projection 25' forms a stop for the pin at the outer region of the bone, and it is clear that three pins inserted in front of or behind a fracture surface in such a manner that one thereof enters on the side into the bone opposite the other two, with their stops 25' prevent mutual displacements between bones and the apparatus along the axis of the pins, and thus even when in the region of the core 32 and/or the thread 33, a clearance between bone and pin should result.

Also shown in FIG. 16 is that on the free end of the shaft 25, the receiving set 25'' is provided to secure the pin to a manual or electrical device for perforating the bone, for example, a drill, whilst at the other end the core 32 supports a receiving cone 32' for a tip adapted as a drill, which may be removed as soon as the pin is secured in the bone.

Figure 18:
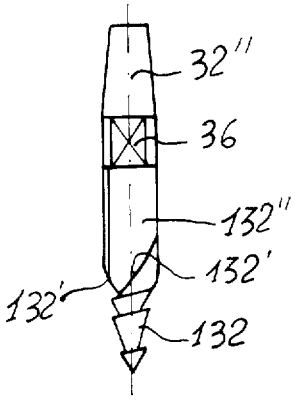
FIG. 18 is a view of a removable tip in the form of an auger.

With reference to FIG. 18, a tip supports a tool cone 32'' which is adapted in form locking manner to the receiving seat 32' and the latching or hooking bore 36 in order to enable it to be inserted in the conical receiving seat 32' by means of rotation with a hook wrench. This tip has the form of an auger and comprises a handle which terminates in a tapered screw 132 which has lateral helical cutting edges 132' with a substantially greater pitch and which define an open cavity 132'' for receiving borings.

It is clear that the cavity 132'' is so dimensioned that it can completely receive the borings and that it may partly also be provided in the interior of the tip itself.

Figure 19:
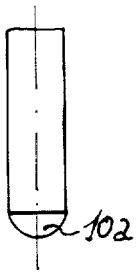
FIGS. 19, 20 and 21 are partial views of three pins which terminate in tips of different shapes.
Figure 20:
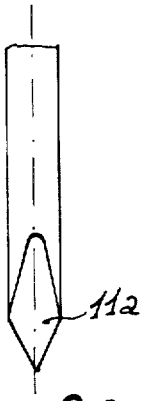
Figure 21:
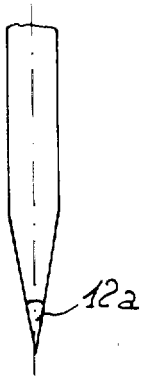
Figure 17:
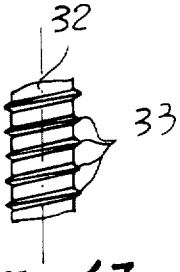
FIG. 17 is a partial view of a part of a pin provided with a thread.

With reference to FIG. 19, it is to be ascertained that a pin terminating in a rounded "tip" 10a can be inserted in a bone only when a corresponding bore has been formed therein prior thereto, whilst the pins in accordance with FIGS. 20 and 21 which terminate in a lance-shaped tip 11a or in a tapered tip 12a may be simply driven in.

Practical tests with pins having a fixed or removable tip, as shown in FIG. 18, have led to excellent results relating to avoiding micro-fractures by screwing in when the depth of thread is 1 mm, and have also led to excellent results with reference to preventing movement relative to the bones and the securing apparatus by stops which have a minimum projection relative to the thread part of 0.5 mm.

We claim:

1. [Apparatus for the external setting or securing of the parts of a fractured bone, said apparatus comprising] *Orthopedic apparatus, comprising* an elongate central body member which is comprised of two *telescopically related* parts adapted to be mutually displaceable parallel to the longitudinal axis of said member and rotatably fixed at all times with respect to each other, [whereby] each part of said central body member [supports] *supporting* a clamping device for pins adapted to be inserted into a part of the bone, further including a pressing and tensioning device in engagement with both said two parts of said central body member, [wherein said two parts of said central body member are telescopically inserted one within the other, wherein] each of said clamping devices [is] *being* mounted on a respective one of said parts of said central body member through a respective ball joint having a center of rotation which substantially lies on the longitudinal axis of said central body member, and securing devices for fixing the mutual rotative position of said parts of said central body member when said two parts of said central body member are being mutually longitudinally displaced and for fixing both the mutual rotative and longitudinal positions of said parts of said central body member after said mutual longitudinal displacement, [wherein] said pressing and tensioning device [is] *being* removably connected to the parts of the central body member, and wherein said pins, at least in the section insertable in the bone, [have] *having* an external thread.

2. Apparatus as recited in claim 1, wherein said parts of said central body member each have free ends, said ends each being connected via a respective one of said ball joints to said clamping devices, whereby a receiving socket for a ball is secured at each end of said central body member, and a threaded ring abutting against said ball is adapted to be screwed onto said socket.

3. Apparatus as recited in claim 2, wherein each clamping device comprises a jaw which is secured to said ball of said joint, and a displaceable jaw which is clampable for securing said pins between said secured and said displaceable jaws.

4. Apparatus as recited in claim 2, wherein said pressing and tensioning device is comprised of two hollow cylinders, which cylinders support bolts projecting substantially at right angles to the longitudinal axes of said cylinders, and which are insertable into cavities which are located proximal to said free ends of said parts; said pressing and tensioning device further including a screw bolt having a head and a shaft, said head abutting against said first hollow cylinder and said shaft passing through said first hollow cylinder and secured to an intermediate sleeve between said hollow cylinders, and having an external threaded section which engages in an internal thread provided in said second hollow cylinder.

5. Apparatus as recited in claim 2, wherein said securing devices of said ball joints each comprise said receiving socket and said threaded ring adapted to be screwed thereon and thereby clamping said ball.

6. Apparatus as recited in claim 5, in which additional securing screws are provided which pass through said threaded ring.

7. Apparatus as recited in claim 1, wherein said pins have a cylindrical shank and a conical core which is provided with a helical outer thread of constant pitch, whereby the outer conicities of said core and said outer thread are parallel.

8. Apparatus as recited in claim 7, in which said cylindrical shank supports a cylindrical outer thread, the pitch of which corresponds to said core thread, and wherein said shank is screwed into a cavity of a support member, the internal thread of which corresponds to the outer thread of the shank.

9. Apparatus as recited in claim 1, wherein said pins have a cylindrical shank and a conical core which bears a cylindrical outer thread of constant pitch.

10. Apparatus as recited in claim 9, in which said cylindrical shank supports a cylindrical outer thread, the pitch of which corresponds to said core thread, and wherein said shank is screwed into a cavity of a support member, the internal thread of which corresponds to the outer thread of the shank.

11. Apparatus as recited in claim 1, wherein said pins have a cylindrical shank and a cylindrical core which has a helical outer thread of constant pitch formed thereon.

12. Apparatus as recited in claim 11, in which said cylindrical shank supports a cylindrical outer thread, the pitch of which corresponds to said core thread, and wherein said shank is screwed into a cavity of a support member, the internal thread of which corresponds to the outer thread of the shank.

13. Apparatus as recited in claim 1, wherein said securing devices for the mutual securing of said two parts of said central body member have at least one screw, by means of which one part of said central body member may be clamped against said other part.

14. Apparatus as recited in claim 1, wherein said free ends of said two parts of said central body member are each connected to said clamping devices via a ball joint, and wherein said securing devices of said ball joints are each comprised of a cylindrical bolt having an eccentric central part passing through a bore of the given end of said central body member, a hemispherical shell or cup for receiving said ball of said joint which is displaceable in a hollow cylindrical section at the end of said central body member and with its lower part supported on said eccentric part of the bolt, a quick-release connector sleeve which is mounted on the hollow cylindrical section and having a ring with a hemispherical surface, and devices to locate said cylindrical bolt in a stable rotary position.

15. Apparatus as recited in claim 14, wherein knurlings are provided on at least one of said ball and the surfaces of said cup and said quick-release connector sleeve.

16. Apparatus as recited in claim 14 wherein said devices for securing said cylindrical bolt are comprised of a set screw which abuts against the eccentric part of said bolt.

17. Apparatus as recited in claim 14, wherein said devices for securing said cylindrical bolt comprise threaded members which exert an axial traction on said bolt, whereby the traction effect is sprung by at least one spring ring.

18. Apparatus as recited in claim 1, wherein said pins have a smooth core extending into a tip, at least a part of said core being provided with a thread which projects radially beyond said core and at least one shank which projects radially slightly beyond said thread.

19. Apparatus as recited in claim 18, further including a removable tip adapted to be connected to one end of a said pin, said removable tip including a core tapering into a point at a forward end thereof and having a conical helical thread which to the rear of said tip merges into a cylindrical section having steep helical cutting surfaces which define a cavity adapted to receive borings formed during a drilling operation.

*20. Orthopedic apparatus, comprising an elongate extendable central body comprised of two parts adapted to be mutually displaceable along the longitudinal axis of said body and retained against relative rotation of said parts, a pin mount connected to each end of said body, a ball joint establishing the connection of each pin mount to said body, with ball-joint centers substantially on said axis, selectively operable means for locking a given extended length of said body, selectively operable means associated with each ball joint for locking a given orientation of the involved pin mount with respect to said body, and selectively operable means including pressing and tensioning means operative between said two parts for controlled length adjustment of said body.*

*21. Apparatus according to claim 20, in which said pressing and tensioning means is removably connected to each of said two parts.*

*22. Apparatus according to claim 20, in which said pressing and tensioning means includes a screw-jack mechanism.*

* * * * *